(12) United States Patent
Suzuki

(10) Patent No.: US 11,814,353 B2
(45) Date of Patent: Nov. 14, 2023

(54) SEPARATION METHOD AND PRODUCTION METHOD OF BRANCHED DIOLEFIN

(71) Applicant: ZEON CORPORATION, Tokyo (JP)

(72) Inventor: Takahiro Suzuki, Tokyo (JP)

(73) Assignee: ZEON CORPORATION, Tokyo (JP)

( * ) Notice: Subject to any disclaimer, the term of this patent is extended or adjusted under 35 U.S.C. 154(b) by 320 days.

(21) Appl. No.: 17/593,149

(22) PCT Filed: Mar. 17, 2020

(86) PCT No.: PCT/JP2020/011804
§ 371 (c)(1),
(2) Date: Sep. 10, 2021

(87) PCT Pub. No.: WO2020/196110
PCT Pub. Date: Oct. 1, 2020

(65) Prior Publication Data
US 2022/0185747 A1 Jun. 16, 2022

(30) Foreign Application Priority Data
Mar. 26, 2019 (JP) .................................. 2019-058893

(51) Int. Cl.
*C07C 7/144* (2006.01)
*B01D 53/22* (2006.01)
*B01D 67/00* (2006.01)
*B01D 71/02* (2006.01)
*C01B 39/20* (2006.01)

(52) U.S. Cl.
CPC ............ *C07C 7/144* (2013.01); *B01D 53/228* (2013.01); *B01D 67/0051* (2013.01); *B01D 71/028* (2013.01); *C01B 39/20* (2013.01); *B01D 2257/702* (2013.01)

(58) Field of Classification Search
CPC .......... C01B 39/20; C07C 7/144; C07C 11/18; B01D 53/228; B01D 71/028; B01D 71/0281; B01D 61/36; B01D 61/366; B01D 67/0051; B01D 69/10; B01D 69/1213; B01D 2257/702
USPC ............... 502/4, 64, 407; 585/601, 818, 820
See application file for complete search history.

(56) References Cited

FOREIGN PATENT DOCUMENTS

JP 2015174081 A 10/2015

OTHER PUBLICATIONS

Machine Translation of WO 2016/084845, (2016), 1-15.*
Sep. 28, 2021, International Preliminary Report on Patentability issued in the International Patent Application No. PCT/JP2020/011804.
Nov. 30, 2022, the Extended European Search Report issued by the European Patent Office in the corresponding European Patent Application No. 20779283.9.

* cited by examiner

*Primary Examiner* — Elizabeth D Wood
(74) *Attorney, Agent, or Firm* — KENJA IP LAW PC

(57) ABSTRACT

A separation method includes a separation step of using a zeolite membrane composite to separate a branched diolefin from a branched hydrocarbon mixture containing the branched diolefin and at least one branched hydrocarbon in which the number of carbon-carbon double bonds is 1 or less and that is of an equivalent carbon number n to the branched diolefin. The zeolite membrane composite used in this step is a zeolite membrane composite that includes a porous support and a FAU-type zeolite membrane formed on at least one surface of the porous support, and in which the FAU-type zeolite membrane is a silylated FAU-type zeolite membrane including a silyl group at the surface thereof.

5 Claims, 1 Drawing Sheet

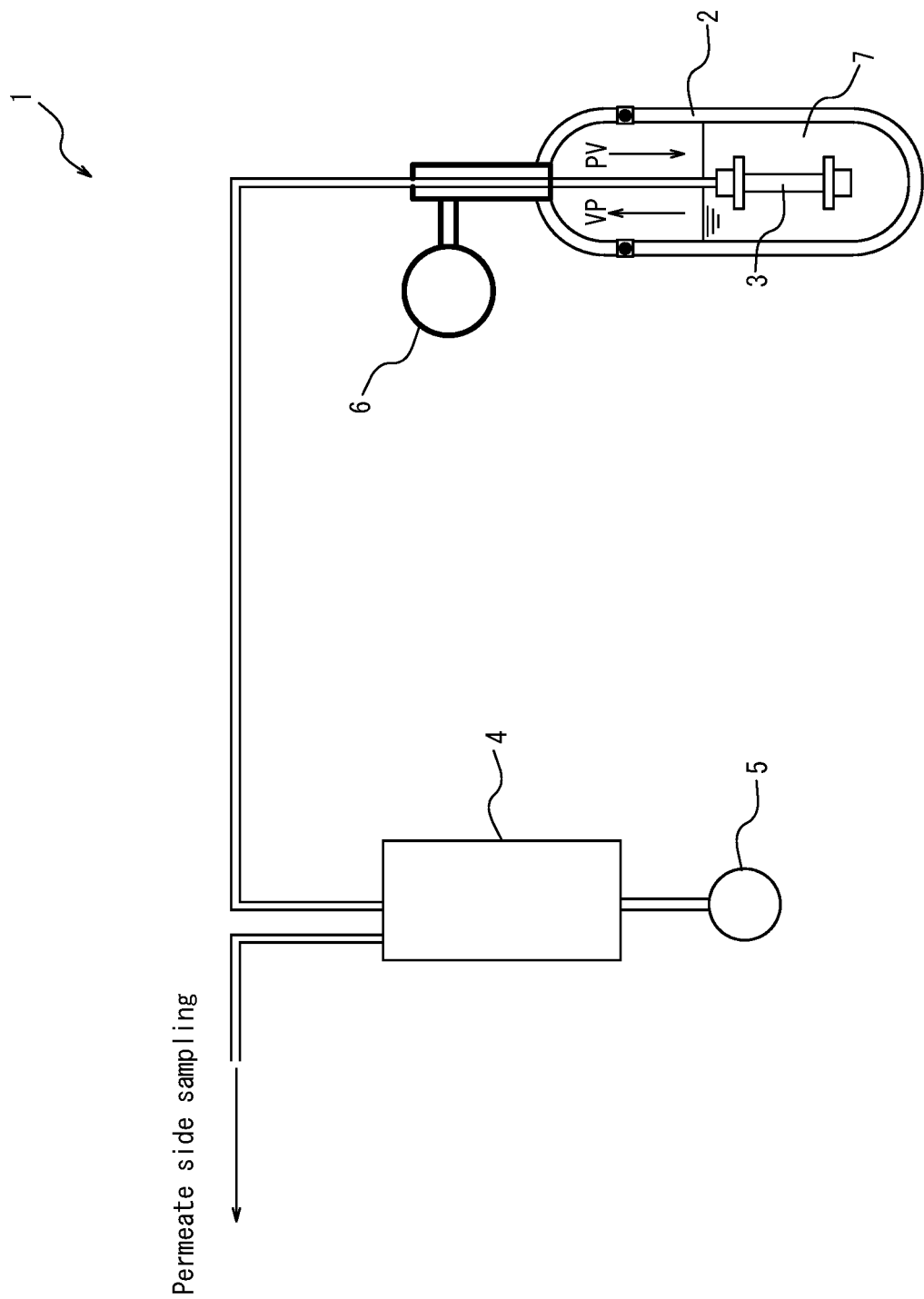

SEPARATION METHOD AND PRODUCTION METHOD OF BRANCHED DIOLEFIN

TECHNICAL FIELD

The present disclosure relates to a separation method and a production method of a branched diolefin, and, in particular, relates to a method of separating a branched diolefin in which a branched diolefin is separated from a branched hydrocarbon mixture through membrane separation using a zeolite membrane composite and to a production method that includes this separation method.

BACKGROUND

Membrane separation is conventionally used as a low-energy method for separating a specific hydrocarbon from a hydrocarbon mixture containing a plurality of hydrocarbons differing in terms of the number of carbon-carbon unsaturated bonds included therein. Zeolite membranes that are obtained by forming a zeolite in a film-like form on a support are widely used as separation membranes.

For example, Patent Literature (PTL) 1 discloses a method of selectively separating an olefin from an olefin/paraffin mixed fluid using a zeolite membrane composite in which a membrane of an X-type zeolite is formed on a porous support. In PTL 1, a Ag-X-type zeolite in which cations of an X-type zeolite that are ion exchangeable have undergone ion exchange with Ag ions is used as the X-type zeolite.

CITATION LIST

Patent Literature

PTL 1: JP2015-174081A

SUMMARY

Technical Problem

The conventional Ag-X-type zeolite described above enables good separation of a paraffin from a monoolefin/paraffin mixed fluid (for example, an ethylene/ethane mixed fluid, an ethylene/propane mixed fluid, a propylene/ethane mixed fluid, or a propylene/propane mixed fluid) as an olefin/paraffin mixed fluid as has been verified in PTL 1. In recent years, there has been a need for a membrane separation technique that enables separation of a branched hydrocarbon including two carbon-carbon unsaturated bonds (i.e., a branched diolefin) from a branched hydrocarbon mixture containing a plurality of branched hydrocarbons that are of equivalent carbon number but differ in terms of the number of carbon-carbon unsaturated bonds included therein.

However, it has not been possible to selectively separate a branched diolefin from a branched hydrocarbon mixture containing a plurality of branched hydrocarbons that are of equivalent carbon number but differ in terms of the number of carbon-carbon unsaturated bonds included therein using the conventional Ag-X-type zeolite described above.

Accordingly, one object of the present disclosure is to provide a method of separating a branched diolefin that enables selective separation of a branched diolefin from a branched hydrocarbon mixture containing a plurality of branched hydrocarbons of equivalent carbon number that differ in terms of the number of carbon-carbon unsaturated bonds included therein.

Another object of the present disclosure is to provide a method of producing a branched diolefin that includes selectively separating a branched diolefin in accordance with a presently disclosed separation method.

Solution to Problem

The inventor conducted diligent studies to achieve these objects. As a result, the inventor reached a new finding that through a zeolite membrane composite obtained by forming a silylated FAU-type zeolite membrane including a silyl group at the surface thereof on a porous support, it is possible to selectively separate a branched diolefin from a branched hydrocarbon mixture containing a plurality of branched hydrocarbons of equivalent carbon number that differ in terms of the number of carbon-carbon unsaturated bonds included therein. The inventor completed the present disclosure based on the new finding set forth above.

Specifically, the present disclosure aims to advantageously solve the problem set forth above, and a presently disclosed method of separating a branched diolefin comprises a separation step of using a zeolite membrane composite to separate a branched diolefin from a branched hydrocarbon mixture containing the branched diolefin and at least one branched hydrocarbon in which the number of carbon-carbon double bonds is 1 or less and that is of an equivalent carbon number n to the branched diolefin, wherein the zeolite membrane composite is a zeolite membrane composite that includes a porous support and a FAU-type zeolite membrane formed on at least one surface of the porous support, and in which the FAU-type zeolite membrane is a silylated FAU-type zeolite membrane including a silyl group at a surface thereof.

By using a zeolite membrane composite that includes a silylated FAU-type zeolite membrane including a silyl group at the surface thereof in the presently disclosed separation method in this manner, it is possible to selectively separate a branched diolefin from a branched hydrocarbon mixture containing a plurality of branched hydrocarbons of equivalent carbon number that differ in terms of the number of carbon-carbon unsaturated bonds included therein.

In the presently disclosed method of separating a branched diolefin, the carbon number n is preferably 4 or 5. In a situation in which a branched hydrocarbon mixture containing a plurality of branched hydrocarbons of an equivalent carbon number n of 4 or 5 that differ in terms of the number of carbon-carbon unsaturated bonds included therein is used as a separation subject in the presently disclosed separation method, the presently disclosed separation method enables selective separation of a branched diolefin.

In the presently disclosed method of separating a branched diolefin, the silyl group is preferably a trimethylsilyl group. By using a zeolite membrane composite that includes a silylated FAU-type zeolite membrane including a trimethylsilyl group at the surface thereof in the presently disclosed separation method, a branched diolefin can be even more selectively separated.

In the presently disclosed method of separating a branched diolefin, in a situation in which the zeolite membrane composite is used to separate a mixture of water and isopropyl alcohol, the zeolite membrane composite preferably has a separation factor $\alpha^W$ of 270 or less as calculated by an equation (A), shown below, $$\alpha^W = (Y_W/Y_1)/(X_W/X_1) \quad \text{(A)}$$

where, in equation (A), $Y_W$ is proportional content of water in a permeate side sample in units of mass %, $Y_1$ is proportional content of isopropyl alcohol in the permeate side sample in units of mass %, $X_W$ is proportional content of water in a separation subject in units of mass %, and $X_1$ is proportional content of isopropyl alcohol in the separation subject in units of mass %.

By using a zeolite membrane composite for which the specific separation factor $\alpha^W$ set forth above is 270 or less in the presently disclosed separation method, a branched diolefin can be even more selectively separated. Note that the mixing ratio of the mixture of water and isopropyl alcohol that is used in measurement of the separation factor $\alpha^W$ is water:isopropyl alcohol=23:77, by mass. Moreover, the temperature condition during measurement of the separation factor $\alpha^W$ is 70° C.

Furthermore, the present disclosure aims to advantageously solve the problem set forth above, and a presently disclosed method of producing a branched diolefin comprises separating the branched diolefin in accordance with any one of the methods of separating a branched diolefin set forth above.

Advantageous Effect

According to the present disclosure, it is possible to provide a method of separating a branched diolefin that enables selective separation of a branched diolefin from a branched hydrocarbon mixture containing a plurality of branched hydrocarbons of equivalent carbon number that differ in terms of the number of carbon-carbon unsaturated bonds included therein.

Moreover, according to the present disclosure, it is possible to produce a branched diolefin through selective separation of the branched diolefin in accordance with the presently disclosed method of separating a branched diolefin.

BRIEF DESCRIPTION OF THE DRAWING

In the accompanying drawing,
FIG. 1 illustrates the schematic configuration of a test apparatus used in examples and comparative examples.

DETAILED DESCRIPTION

The following provides a detailed description of embodiments of the present disclosure.

The presently disclosed separation method is used in separation of a branched diolefin from a branched hydrocarbon mixture containing a plurality of branched hydrocarbons of equivalent carbon number that differ in terms of the number of carbon-carbon unsaturated bonds included therein.

(Method of Separating Branched Diolefin)

The presently disclosed method of separating a branched diolefin is a separation method that includes a separation step of using a zeolite membrane composite to separate a branched diolefin from a branched hydrocarbon mixture containing the branched diolefin and at least one branched hydrocarbon in which the number of carbon-carbon double bonds is 1 or less and that is of an equivalent carbon number n to the branched diolefin. A feature of the zeolite membrane composite used in this step is that it is a zeolite membrane composite that includes a porous support and a FAU-type zeolite membrane formed on at least one surface of the porous support, and in which the FAU-type zeolite membrane is a silylated FAU-type zeolite membrane including a silyl group at the surface thereof.

As a result of a zeolite membrane composite that includes a silylated FAU-type zeolite membrane including a silyl group at the surface thereof being used in the presently disclosed method of separating a branched diolefin, the presently disclosed method of separating a branched diolefin enables separation of a branched diolefin from a branched hydrocarbon mixture containing the branched diolefin and at least one branched hydrocarbon in which the number of carbon-carbon double bonds is 1 or less and that is of an equivalent carbon number n to the branched diolefin. Although the reason for this is not clear, it is presumed to be as follows.

Various types of zeolite membranes that have conventionally been used in membrane separation display separation performance by causing a specific substance contained in a separation subject to pass through pores of the zeolite and causing other substances contained in the separation subject to not pass through the pores. The zeolite membrane composite adopted in the presently disclosed separation method is a zeolite membrane composite that includes a silyl group at the surface thereof. This silyl group not only imparts water repellency to the zeolite membrane composite, but also can itself act as a steric hinderance at the surface of the composite, in the pores of the zeolite, and in proximity thereto. A branched diolefin is thought to selectively pass through the specific zeolite membrane composite set forth above as a result of a combination of an attribute of water repellency that can be imparted to the zeolite membrane composite through the silyl group, a structural feature brought about by a silyl group being present at a zeolite membrane surface having a FAU-type crystal structure, and so forth.

<Separation Step>

In the separation step, the zeolite membrane composite is used to separate a branched diolefin from a branched hydrocarbon mixture containing the branched diolefin and at least one branched hydrocarbon in which the number of carbon-carbon double bonds is 1 or less and that is of an equivalent carbon number n to the branched diolefin.

<<Branched Hydrocarbon Mixture>>

The branched hydrocarbon mixture can contain branched diolefins, branched monoolefins, and branched alkanes of an equivalent carbon number n to one another, and can also contain other hydrocarbons. Note that the carbon number n is an integer, is preferably 4 or 5, and is more preferably 5. In more detail, the branched hydrocarbon mixture contains a branched diolefin of the carbon number n and either or both of a branched monoolefin of the carbon number n and a branched alkane of the carbon number n as main components, and may further contain a hydrocarbon of any carbon number. Note that when the branched hydrocarbon mixture is said to "contain a branched diolefin of the carbon number n and either or both of a branched monoolefin of the carbon number n and a branched alkane of the carbon number n as main components", this means that the branched hydrocarbon mixture contains 50 mass % or more, in total, of a branched diolefin of the carbon number n and either or both of a branched monoolefin of the carbon number n and a branched alkane of the carbon number n. For example, in a case in which the carbon number n of the branched hydrocarbon mixture is 5, the branched hydrocarbon mixture may contain isoprene (number of carbon-carbon double bonds: 2) and may also contain either or both of isopentane (number of carbon-carbon double bonds: 0) and a compound in which the number of carbon-carbon double bonds is 1, such as 2-methyl-1-butene, 2-methyl-2-butene, or 3-methyl-1-butene, and the total proportion constituted thereby in the overall branched hydrocarbon mixture may be 50 mass % or more.

<<Zeolite Membrane Composite>>

The zeolite membrane composite used for separating a branched hydrocarbon mixture such as described above is a zeolite membrane that includes a porous support and a FAU-type zeolite membrane formed on at least one surface of the porous support. A feature of the FAU-type zeolite membrane is that it is a silylated FAU-type zeolite membrane including a silyl group at the surface thereof.

Porous Support

In the zeolite membrane composite, the porous support that supports a zeolite membrane on at least one surface thereof is a porous body that includes a plurality of pores. The porous support may have any shape such as a flat film shape, a flat plate shape, a tube shape, or a honeycomb shape without any specific limitations. The material of the porous support is not specifically limited and may be a support that is a porous body formed of a porous ceramic such as alumina, mullite, zirconia, cordierite, or silicon carbide; a glass such as shirasu porous glass; or a porous sintered metal such as stainless steel. The average pore diameter of the porous support can be not less than 100 nm and not more than 5 μm, for example.

Zeolite Membrane

The zeolite membrane is a membrane obtained through silylation of a FAU-type zeolite membrane. In other words, the zeolite membrane is a silylated FAU-type zeolite membrane. A FAU-type zeolite is a zeolite that has a faujasite (FAU) crystal structure. A FAU-type crystal structure is defined in a database provided by the International Zeolite Association. The term "FAU-type zeolite membrane" as used in the present specification means that the zeolite membrane contains a FAU-type zeolite, preferably that more than 50 mass % of zeolite forming the zeolite membrane is a FAU-type zeolite, and more preferably that all zeolite forming the zeolite membrane is a FAU-type zeolite.

The thickness of the zeolite membrane can be not less than 1 μm and not more than 50 μm, for example. A zeolite membrane composite in which the thickness of the zeolite membrane is within the range set forth above enables even more selective separation of a branched diolefin.

The "thickness of the zeolite membrane" can be measured using a scanning electron microscope (SEM). The thickness of the zeolite membrane can be controlled by, for example, adjusting the average particle diameter of seed crystals used to form the zeolite membrane, the synthesis conditions of the zeolite (temperature, time, etc.), and so forth.

The zeolite membrane composite can be produced through a seed crystal adhesion step of adhering zeolite seed crystals to the porous support to obtain a seed crystal-bearing support, a zeolite membrane formation step of forming a zeolite membrane formed of a zeolite on the seed crystal-bearing support, and a silylation step of performing silylation treatment of the zeolite membrane.

Operations in each of these steps can be performed in accordance with a known zeolite membrane formation method without any specific limitations.

In the seed crystal adhesion step, zeolite seed crystals may be adhered to (mounted on) the porous support by a known technique such as coating or rubbing. More specifically, FAU-type zeolite seed crystals may be adhered to the porous support in the seed crystal adhesion step by applying, onto the porous support, a dispersion liquid obtained by dispersing FAU-type zeolite seed crystals in water, and then drying the dispersion liquid that has been applied.

Note that the FAU-type zeolite seed crystals may be a commercially available FAU-type zeolite or may be produced in accordance with a known method. Also note that the FAU-type zeolite may be subjected to micronization or the like as necessary.

In the zeolite membrane formation step, the porous support to which the FAU-type zeolite seed crystals have been adhered is immersed in an aqueous sol containing a silica source, a mineralizer, an aluminum source, and so forth, and a zeolite membrane containing a FAU-type zeolite is synthesized by hydrothermal synthesis. The porous support including the zeolite membrane obtained in the zeolite membrane formation step may optionally be subjected to a boil washing operation and/or a firing operation.

The silica source may be colloidal silica, wet silica, amorphous silica, fumed silica, sodium silicate, silica sol, silica gel, kaolinite, diatomite, white carbon black, tetrabutoxysilane, tetrabutyl orthosilicate, tetraethoxysilane, or the like, for example, without any specific limitations. Of these silica sources, colloidal silica can suitably be used.

The mineralizer may be NaOH or the like, for example, without any specific limitations.

The aluminum source may be $NaAlO_2$ or $Al(OH)_3$, for example, without any specific limitations. Of these aluminum sources, $NaAlO_2$ can suitably be used.

Although no specific limitations are placed on the mixing ratio of various compounding agents in production of the aqueous sol used in the zeolite membrane formation step, the mixing ratio of silica source:aluminum source, as a molar ratio, is preferably 1:0.08 to 1:1.0.

The method by which the porous support having FAU-type zeolite seed crystals adhered thereto is immersed in the aqueous sol is not specifically limited and may, for example, be a method in which the aqueous sol is loaded into a pressure-resistant vessel housing the porous support having FAU-type zeolite seed crystals adhered thereto. Alternatively, a method in which the porous support having FAU-type zeolite seed crystals adhered thereto is loaded into a pressure-resistant vessel housing the aqueous sol may be adopted.

The heating temperature during heating of the aqueous sol in which the porous support having FAU-type zeolite seed crystals adhered thereto is immersed and synthesis of a FAU-type zeolite by hydrothermal synthesis to form a zeolite membrane on the porous support is preferably not lower than 50° C. and not higher than 250° C., and more preferably not lower than 70° C. and not higher than 200° C. The heating time is preferably not less than 1 hour and not more than 50 hours, and more preferably not less than 2 hours and not more than 20 hours. Examples of methods by which the aqueous sol and the porous support in the pressure-resistant vessel can be heated include a method in which the pressure-resistant vessel is heated in a hot-air dryer and a method in which the pressure-resistant vessel is heated by a directly attached heater. Once hydrothermal synthesis has ended, the porous support including the obtained zeolite membrane may be subjected to brushing. This brushing can remove amorphous material adhered to the zeolite membrane obtained as a result of hydrothermal synthesis. The selectivity of separation by the zeolite membrane can be further increased by performing brushing.

In a situation in which the porous support including the zeolite membrane obtained as described above is subjected to boil washing, the washing liquid may be distilled water, for example. The boil washing time is preferably not less than 10 minutes and not more than 2 hours, and more preferably not less than 30 minutes and not more than 1.5 hours. Note that the boil washing may be repeated (for example, 2 or 3 times) and that the repetitions of the boil washing may each be carried out under the same boil washing conditions or different boil washing conditions. Drying treatment may be performed after the boil washing as necessary. The drying temperature of the porous support including the zeolite membrane after boil washing is preferably 70° C. or higher, and is preferably 200° C. or lower, and more preferably 180° C. or lower. Moreover, the drying time can be not less than 1 hour and not more than 48 hours, for example.

In the silylation step, the zeolite membrane that has been formed on the porous support is treated with a silylating agent. The silylating agent may be hexamethyldisilazane, trimethylchlorosilane, dimethyldichlorosilane, or the like. Moreover, the silylating agent preferably does not include a halogen atom, and, of the silylating agents listed above, is particularly preferably hexamethyldisilazane. In a case in which hexamethyldisilazane is used as the silylating agent, the resultant silylated zeolite membrane includes a trimethylsilyl group as a silyl group. The lack of a halogen atom in the silylating agent can inhibit degradation of the zeolite membrane caused by the silylation treatment. The method of silylation treatment is not specifically limited and may be gas-phase silylation that involves bringing the zeolite membrane into contact with a silylating agent that is in a vapor state or liquid-phase silylation that involves bringing the zeolite membrane into contact with a silylating agent that is in a liquid state.

More specifically, the gas-phase silylation involves implementing a vaporization step of vaporizing a silylating agent by a known vaporization method such as bubbling and a vapor contact step of bringing the zeolite membrane into contact with vapor of the silylating agent obtained in the vaporization step. The contact time in the gas-phase silylation can be not less than 12 hours and not more than 24 hours, for example.

The liquid-phase silylation involves implementing an immersion step of immersing the zeolite membrane in a liquid that contains a silylating agent. The liquid containing a silylating agent may be a liquid composed of only a liquid silylating agent or may be a solution containing a silylating agent and a solvent. A known solvent can be used as the solvent without any specific limitations. The immersion time in the liquid-phase silylation can be not less than 12 hours and not more than 24 hours, for example.

It is preferable that liquid-phase silylation is adopted as the method of silylation treatment of the zeolite membrane. By implementing the membrane separation step using a silylated zeolite membrane that has been silylated in a liquid phase, it is possible to lengthen the period of time for which the zeolite membrane can be used without replacement, cleaning, regeneration, or the like, and thus it is possible to perform membrane separation with high sustainability.

In a situation in which the zeolite membrane composite including the silylated FAU-type zeolite membrane is used to separate a mixture of water and isopropyl alcohol, the zeolite membrane composite preferably has a separation factor $\alpha^W$ of 270 or less as calculated by equation (A), shown below.

$$\alpha^W = (Y_W/Y_1)/(X_W/X_1) \quad (A)$$

(In equation (A), $Y_W$ is proportional content [mass %] of water in a permeate side sample, $Y_1$ is proportional content [mass %] of isopropyl alcohol in the permeate side sample, $X_W$ is proportional content [mass %] of water in a separation subject, and $X_1$ is proportional content [mass %] of isopropyl alcohol in the separation subject.)

The separation factor $\alpha^W$ is more preferably 250 or less, and even more preferably 230 or less. When the separation factor $\alpha^W$ measured for the zeolite membrane composite is 270 or less (or is 250 or less, or 230 or less), a branched diolefin can be even more selectively separated. A smaller value for the separation factor $\alpha^W$ indicates that the zeolite membrane composite has higher water repellency.

<<Supplementary Description>>

The separation step can be implemented by vapor permeation (VP), pervaporation (PV), or the like without any specific limitations. Of these methods, PV is preferable from a viewpoint of increasing the separation factor. The separation step is preferably carried out under heated conditions. Specifically, the separation step can be carried out under conditions of preferably not lower than 20° C. and not higher than 300° C., more preferably not lower than 25° C. and not higher than 250° C., and even more preferably not lower than 50° C. and not higher than 200° C.

The separation step may be performed repeatedly. In other words, separated material obtained through an $m^{th}$ separation step may be subjected to an $(m+1)^{th}$ separation step. By using obtained separated material as a separation subject for a further separation step, it is possible for a higher overall separation selectivity to be displayed than the separation selectivity that can be obtained when the separation step is performed just once. The number of repetitions of the separation step that are implemented can be freely set, for example, in accordance with a separation factor $\alpha^d$, which can be calculated by a method described in the EXAMPLES section of the present specification.

(Method of Producing Branched Diolefin)

The presently disclosed method of producing a branched diolefin includes separating a branched diolefin from a specific branched hydrocarbon mixture in accordance with the presently disclosed method of separating a branched diolefin set forth above. In the presently disclosed method of producing a branched diolefin, a branched diolefin can be separated by membrane separation, and thus the branched diolefin can be produced with low-energy (i.e., can be produced efficiently) compared to a conventional method. The specific branched hydrocarbon mixture is a mixture containing a branched diolefin and at least one branched hydrocarbon in which the number of carbon-carbon double bonds is 1 or less and that is of an equivalent carbon number n to the branched diolefin as previously described. Details pertaining to this mixture are as previously described in detail in the "Branched hydrocarbon mixture" section. Moreover, operations previously described in detail in the "Separation step" section can suitably be performed in separation of the branched diolefin. The presently disclosed method of producing a branched diolefin may include a purification step of purifying the obtained branched diolefin, implemented at a later stage than the separation step. Examples of purification steps that can be implemented include, but are not specifically limited to, steps that are performed by distillation and chromatographic separation.

EXAMPLES

The following provides a more specific description of the present disclosure based on examples. However, the present disclosure is not limited to the following examples. In the following description, "%" and the like used to express quantities are by mass, unless otherwise specified.

In the examples and comparative examples, analysis of an obtained zeolite membrane composite was performed by a method described below, and separation performance was calculated by a method described below.

<Analysis of Zeolite Membrane Composite>
<<X-Ray Diffraction Pattern>>

An X-ray diffractometer (Discover D8 produced by Bruker AXS) was used to obtain an X-ray diffraction pattern of a porous separation layer. The measurement conditions were as follows.

X-ray source: Cu-Kα radiation
Wavelength λ: 1.54 Angstroms
Tube voltage: 30 kV
Tube current: 15 mA
Power: 0.9 kW
Incident slit: Length 1.0 mm×width 1.0 mm
Receiving slit: Soller slit (angular resolution 0.35 deg)
Detector: Scintillation counter
Measurement rate: 0.01 deg/s <Separation Performance>

The results of a separation test were used to calculate the permeation flux F using the following equation (I). The separation factor $\alpha^d$ was calculated using the following equation (II). Note that a hydrocarbon mixture of isopentane (branched alkane having carbon number of 5) and isoprene (branched diolefin having carbon number of 5) was used as a separation subject.

$$F = W/(A \times t) \quad (I)$$

$$\alpha^d = (Y_d/Y_a)/(X_d/X_a) \quad (II)$$

In equation (I), W is the mass [kg] of permeate that has passed through the zeolite membrane composite, A is the effective area [m²] of the zeolite membrane composite, and t is the processing time [h]. In equation (II), $Y_d$ is the proportional content [mass %] of isoprene in a permeate side sample, $Y_a$ is the proportional content [mass %] of isopentane in the permeate side sample, $X_d$ is the proportional content [mass %] of isoprene in the separation subject, and $X_a$ is the proportional content [mass %] of isopentane in the separation subject.

A larger value for the separation factor α indicates that the zeolite membrane composite has higher isoprene selectivity.

Example 1

<Seed Crystal Adhesion Step>

FAU-type zeolite seed crystals (HSZ-320NAA produced by Tosoh Corporation) were applied onto a tube-shaped porous α-alumina support (external diameter: 2.5 mm; average pore diameter: 150 nm) serving as a porous support by a coating method and were dried to obtain a porous support having FAU-type zeolite seed crystals adhered thereto (hereinafter, referred to as a "seed crystal-bearing support").

<Zeolite Membrane Formation Step>

Stirring of 3.29 g of NaOH as a mineralizer, 0.06 g of NaAlO₂ as an aluminum source, 7.40 g of colloidal silica as a silica source, and 46.39 g of ultrapure water was performed at 25° C. for 3 hours. This operation yielded an aqueous sol for zeolite membrane formation. The composition of the aqueous sol, as a molar ratio, was SiO₂:Al₂O₃:Na₂O:H₂O=12.8:1:17:975.

The aqueous sol obtained as described above was loaded into a pressure-resistant synthesis vessel. Next, the seed crystal-bearing support obtained in the seed crystal adhesion step was immersed in the aqueous sol inside the pressure-resistant synthesis vessel, and a reaction (hydrothermal synthesis) was carried out at 85° C. for 6 hours to form a zeolite membrane on the porous support. The porous support including the obtained zeolite membrane was subjected to brushing and was subsequently dried for 12 hours in an 85° C. thermostatic dryer.

<Silylation Step>

Hexamethyldisilazane was used as a silylating agent. The porous support including the zeolite membrane obtained as described above was loaded into a glass tube containing 1,1,1,3,3,3-hexamethyldisilazane under conditions of 25° C., and the glass tube was stoppered with nitrogen enclosed therein. The porous support including the zeolite membrane was pulled out after being immersed at 25° C. for 24 hours and was then dried at 250° C. for 12 hours in a muffle furnace to obtain a zeolite membrane composite including a silylated FAU-type zeolite membrane that had been silylated in a liquid phase.

The zeolite membrane composite including the silylated FAU-type zeolite membrane that was obtained by the step described above was measured by X-ray diffraction to obtain an X-ray diffraction pattern. The zeolite membrane was confirmed to have a FAU-type structure based on the obtained X-ray diffraction pattern.

<Separation Test>

The zeolite membrane composite including the silylated FAU-type zeolite membrane obtained as described above was used to perform a separation test using a test apparatus 1 such as illustrated in FIG. 1.

<<Test Apparatus>>

The test apparatus 1 illustrated in FIG. 1 includes a feedstock tank 2, a zeolite membrane composite 3, and a cold trap 4. The test apparatus 1 also includes a vacuum pump 5 downstream of the cold trap 4. The internal pressure of the feedstock tank 2 is controlled to a pressure indicated by a pressure gauge 6 through adjustment of the external temperature. Moreover, the zeolite membrane composite 3 inside the feedstock tank 2 is moved by a control mechanism (not illustrated) such as to be in contact with a liquid phase or gas phase hydrocarbon mixture 7. The zeolite membrane composite 3 illustrated in FIG. 1 is a tubular body, and a permeate that selectively passes through the zeolite membrane penetrates to the inside of the tube.

In the test apparatus 1, the permeate side of the zeolite membrane composite 3 is placed in a reduced pressure state by the vacuum pump 5 such that a permeate that has passed through the zeolite membrane composite 3 is fed to the cold trap 4. Permeate that has been restored to a liquid phase through cooling by the cold trap 4 can be extracted as a permeate side sample.

<<Membrane Separation>>

The separation test was implemented as follows using the test apparatus 1 illustrated in FIG. 1.

Specifically, a hydrocarbon mixture containing 50 mass % each of isoprene and isopentane was first loaded into the feedstock tank 2 and was then heated to 70° C. by a heating mechanism (not illustrated). The zeolite membrane composite 3 was then moved by the control mechanism (not illustrated) such that the liquid phase hydrocarbon mixture was in contact with the zeolite membrane composite 3. The vacuum pump 5 located downstream of the cold trap 4 was used to place the permeate side in a reduced pressure state (3 kPaA). In other words, in Example 1, separation performance was evaluated for a case in which the separation step was performed by pervaporation (PV). Permeate (gas phase)

that had passed through the zeolite membrane composite 3 was restored to a liquid phase through cooling by the cold trap 4, and permeate that passed for 30 minutes from the start of separation was sampled. The mass of the permeate side sample that had been taken was measured. Moreover, the concentrations (mass %) of isoprene and isopentane in the permeate side sample were measured using a gas chromatograph. These measured values were used to determine values for the separation factor α and the permeation flux F. The results are shown in Table 1.

<Separation Factor $\alpha^W$ of Water>

Membrane separation of a mixture of water and isopropyl alcohol in a volume ratio of 23:77 was performed using a zeolite membrane composite including a silylated FAU-type zeolite membrane that was separately produced by performing operations in the seed crystal adhesion step through to the silylation step described above. The conditions of the separation test were the same as previously described in the "Membrane separation" section with the exception that the mixture of water and isopropyl alcohol in a volume ratio of 23:77 was used as a separation subject. The results of the separation test were used to calculate the separation factor $\alpha^W$ by the following equation (A). The result is shown in Table 1.

$$\alpha^W = (Y_W/Y_1)/(X_W/X_1) \quad (A)$$

(In equation (A), $Y_W$ is proportional content [mass %] of water in the permeate side sample, $Y_1$ is proportional content [mass %] of isopropyl alcohol in the permeate side sample, $X_W$ is proportional content [mass %] of water in the separation subject, and $X_1$ is proportional content [mass %] of isopropyl alcohol in the separation subject.)

Example 2

Separation performance was evaluated for a case in which the separation step was performed by vapor permeation (VP). With regards to the specific operations, the zeolite membrane composite 3 was moved by the control mechanism (not illustrated) such that a gas phase hydrocarbon mixture was in contact with the zeolite membrane composite 3 in the operations described in the "Membrane separation" section. With the exception of this point, a separation test was performed, and values for the separation factor α and the permeation flux F were determined in the same way as in Example 1. The results are shown in Table 1.

Comparative Example 1

A zeolite membrane composite was obtained in the same way as in Example 1 with the exception that the silylation step was not performed, and the obtained zeolite membrane composite was used to perform a separation test in the same way as in Example 1. In other words, in Comparative Example 1, a separation test was performed by PV using a zeolite membrane composite including a FAU-type zeolite membrane that was not silylated. Obtained values for the separation factor α and the permeation flux F are shown in Table 1.

Moreover, the separation test described in the "Separation factor $\alpha^W$ of water" section of Example 1 was performed to determine the separation factor $\alpha^W$ for a zeolite membrane composite that was obtained in the same way as in Example 1 with the exception that the silylation step was not performed. The result is shown in Table 1.

Comparative Example 2

A zeolite membrane composite was obtained in the same way as in Example 1 with the exception that the silylation step was not performed, and the obtained zeolite membrane composite was used to perform a separation test in the same way as in Example 2. In other words, in Comparative Example 2, a separation test was performed by VP using a zeolite membrane composite including a FAU-type zeolite membrane that was not silylated. Obtained values for the separation factor $\alpha^d$ and the permeation flux F are shown in Table 1.

Comparative Example 3

A zeolite membrane composite was obtained in the same way as in Example 1 with the exception that operations differing as described below were performed in the various steps. The obtained zeolite membrane composite was used to perform a separation test in the same way as in Example 2. In other words, in Comparative Example 3, a separation test was performed by VP using a zeolite membrane composite that included a silylated MOR-type zeolite membrane. Obtained values for the separation factor $\alpha^d$ and the permeation flux F are shown in Table 1.

Operations performed in various steps that differ from Example 1

MOR-type zeolite seed crystals (NSZ-642NAA produced by Tosoh Corporation) were used as zeolite seed crystals in the seed crystal adhesion step.

In the zeolite membrane formation step, 2.16 g of NaOH as a mineralizer, 0.09 g of $NaAlO_2$ as an aluminum source, 20.13 g of colloidal silica as a silica source, and 34.77 g of ultrapure water were stirred at 50° C. for 4 hours to yield an aqueous sol for zeolite membrane formation. The composition of this aqueous sol, as a molar ratio, was $SiO_2:NaO_2:Al_2O_3:H_2O=36:10:0.2:960$. The hydrothermal synthesis temperature and time were 165° C. and 6 hours, respectively. The porous support including the zeolite membrane obtained through hydrothermal synthesis was subjected to brushing, and was then subjected to 60 minutes of boil washing in boiled distilled water and 12 hours of drying in an 85° C. thermostatic dryer.

The obtained zeolite membrane composite was confirmed to be a MOR-type upon being analyzed as previously described.

Moreover, the separation test described in the "Separation factor $\alpha^W$ of water" section of Example 1 was performed to determine the separation factor $\alpha^W$ for the obtained zeolite membrane composite. The result is shown in Table 1.

Comparative Example 4

Operations were performed in the same way as in Comparative Example 3 with the exception that the heating temperature of the feedstock tank in the separation test was changed to 50° C. Obtained values for the separation factor $\alpha^d$ and the permeation flux F are shown in Table 1.

TABLE 1

| | | | Example 1 | Example 2 | Comparative Example 1 | Comparative Example 2 | Comparative Example 3 | Comparative Example 4 |
|---|---|---|---|---|---|---|---|---|
| Separation subject | Carbon number n [carbons] | | 5 | 5 | 5 | 5 | 5 | 5 |
| | Type of branched diolefin | | Isoprene | Isoprene | Isoprene | Isoprene | Isoprene | Isoprene |
| | Type of branched alkane | | Isopentane | Isopentane | Isopentane | Isopentane | Isopentane | Isopentane |
| Zeolite membrane composite | Porous support | Pore diameter [nm] | 150 | 150 | 150 | 150 | 150 | 150 |
| | | Material | α Alumina | α Alumina | α Alumina | α Alumina | α Alumina | α Alumina |
| | Zeolite membrane | Type of zeolite | FAU | FAU | FAU | FAU | MOR | MOR |
| | | Silylation | Yes | Yes | No | No | Yes | Yes |
| | | Separation factor $\alpha^W$ | 211 | 211 | 284 | 284 | 37.4 | 37.4 |
| Separation step | Separation method | | PV | VP | PV | VP | VP | VP |
| | Temperature [° C.] | | 70 | 70 | 70 | 70 | 70 | 50 |
| Separation performance | Permeation flux F [kg/m²/h] | | 0.0873 | 0.0691 | 0.0715 | 0.0944 | 0.133 | 0.0934 |
| | Separation factor $\alpha^d$ [—] | | 1.59 | 1.25 | 0.904 | 0.797 | 0.862 | 0.719 |

It can be seen from Table 1 that through the separation methods of Examples 1 and 2 in which a zeolite membrane composite including a silylated FAU-type zeolite membrane was used, the value of the separation factor $\alpha^d$ was large, and isoprene (branched diolefin) could be selectively separated from a branched hydrocarbon mixture containing isoprene and isopentane. In contrast, it can be seen that in the separation methods of Comparative Examples 1 and 2 in which a zeolite membrane composite including a non-silylated FAU-type zeolite membrane was used and Comparative Examples 3 and 4 in which a zeolite membrane composite including a silylated MOR-type zeolite membrane was used, the value of the separation factor $\alpha^d$ was smaller than in the examples, and isoprene could not be selectively separated.

INDUSTRIAL APPLICABILITY

According to the present disclosure, it is possible to provide a method of separating a branched diolefin that enables selective separation of a branched diolefin from a branched hydrocarbon mixture containing a plurality of branched hydrocarbons of equivalent carbon number that differ in terms of the number of carbon-carbon unsaturated bonds included therein.

Moreover, it is possible to produce a branched diolefin through selective separation of the branched diolefin in accordance with the presently disclosed method of separating a branched diolefin.

REFERENCE SIGNS LIST 1 test apparatus
2 feedstock tank
3 zeolite membrane composite
4 cold trap
5 vacuum pump
6 pressure gauge
7 hydrocarbon mixture

The invention claimed is:

1. A method of separating a branched diolefin comprising a separation step of using a zeolite membrane composite to separate a branched diolefin from a branched hydrocarbon mixture containing the branched diolefin and at least one branched hydrocarbon in which the number of carbon-carbon double bonds is 1 or less and that is of an equivalent carbon number n to the branched diolefin, wherein
the zeolite membrane composite is a zeolite membrane composite that includes a porous support and a FAU-type zeolite membrane formed on at least one surface of the porous support, and in which the FAU-type zeolite membrane is a silylated FAU-type zeolite membrane including a silyl group at a surface thereof.

2. The method of separating a branched diolefin according to claim 1, wherein the carbon number n is 4 or 5.

3. The method of separating a branched diolefin according to claim 1, wherein the silyl group is a trimethylsilyl group.

4. The method of separating a branched diolefin according to claim 1, wherein
in a situation in which the zeolite membrane composite is used to separate a mixture of water and isopropyl alcohol, the zeolite membrane composite has a separation factor $\alpha^W$ of 270 or less as calculated by an equation (A), shown below, $$\alpha^W = (Y_W/Y_1)/(X_W/X_1) \tag{A}$$

where, in equation (A), $Y_W$ is proportional content of water in a permeate side sample in units of mass %, $Y_1$ is proportional content of isopropyl alcohol in the permeate side sample in units of mass %, $X_W$ is proportional content of water in a separation subject in units of mass %, and $X_1$ is proportional content of isopropyl alcohol in the separation subject in units of mass %.

5. A method of producing a branched diolefin comprising separating the branched diolefin in accordance with the method of separating a branched diolefin according to claim 1.

* * * * *